United States Patent
Kellogg, Jr.

(10) Patent No.: US 10,071,177 B1
(45) Date of Patent: Sep. 11, 2018

(54) HOSPITAL AND OPERATING ROOM DESIGNS AND STERILIZATION METHODS

(71) Applicant: SYNERGY MED GLOBAL DESIGN SOLUTIONS, LLC (a Delaware LLC), Golden, CO (US)

(72) Inventor: Sanford M. Kellogg, Jr., Golden, CO (US)

(73) Assignee: SYNERGY MED GLOBAL DESIGN SOLUTIONS, LLC, Golden, CO (US)

( * ) Notice: Subject to any disclaimer, the term of this patent is extended or adjusted under 35 U.S.C. 154(b) by 234 days.

(21) Appl. No.: 15/236,888

(22) Filed: Aug. 15, 2016

(51) Int. Cl.
*A61L 9/00* (2006.01)
*A61L 2/00* (2006.01)
(Continued)

(52) U.S. Cl.
CPC ............... *A61L 2/208* (2013.01); *A61L 2/24* (2013.01); *A61L 9/04* (2013.01); *A61L 9/20* (2013.01); *F24F 3/161* (2013.01); *F24F 7/10* (2013.01); *F24F 11/30* (2018.01); *F24F 11/75* (2018.01); *F24F 11/77* (2018.01); *F24F 13/10* (2013.01); *A61L 2202/11* (2013.01); *A61L 2202/14* (2013.01); *A61L 2202/25* (2013.01); *A61L 2209/111* (2013.01); *A61L 2209/135* (2013.01); *F24F 2003/1614* (2013.01); *F24F 2003/1628* (2013.01); *F24F 2003/1667* (2013.01);
(Continued)

(58) Field of Classification Search
CPC .. A61L 9/20; A61L 9/16; E04F 13/074; E04B 9/003

USPC ............. 422/1, 4, 24, 28, 30; 95/90, 273; 454/187, 188, 228
See application file for complete search history.

(56) References Cited

U.S. PATENT DOCUMENTS 6,132,309 A   10/2000  Panelli et al.
7,125,332 B2  10/2006  Beaver et al.
(Continued)

OTHER PUBLICATIONS

Precision Air Products Co., "LifeSuite Surgical Cleanroom", Form SLS004, (c) 2014 Precision Air Products, uploaded from http://www.precisionairproducts.com/docs/LIFESuite2014.pdf on Jul. 17, 2016.
(Continued)

*Primary Examiner* — Monzer R Chorbaji
(74) *Attorney, Agent, or Firm* — Stephen E. Zweig

(57) ABSTRACT

System and method to reducing risk of patient infections (HAI), using operating rooms equipped with suitable automatic airborne sterilizing agent generators, sensors, mechanisms, automatic air control devices, and ceiling mounted structures that allows the room to both provide air curtains of laminar flow sterilized air over the operating table, as well as to be quickly and completely sterilized. After suitable safety checks, the system isolates the interior air from external air, and activates an air phase anti-microbial agent generator, filing the room with air-phase anti-microbial agent. After sterilization, the invention deactivates the generator, removes the remaining air-phase anti-microbial agent by flowing room air through a catalytic converter, and then restores the connection to outside sterilized air. The ceiling mounted structure is configured for laminar flow air curtain delivery, supply lighting, and support boom mounted operating room equipment. Various sensors, control methods, wall coverings, and other options are disclosed.

20 Claims, 9 Drawing Sheets

(51) Int. Cl.

| | | |
|---|---|---|
| B01L 1/04 | (2006.01) | |
| B01D 53/02 | (2006.01) | |
| A61L 2/20 | (2006.01) | |
| A61L 2/24 | (2006.01) | |
| A61L 9/04 | (2006.01) | |
| A61L 9/20 | (2006.01) | |
| F24F 13/10 | (2006.01) | |
| F24F 7/10 | (2006.01) | |
| F24F 3/16 | (2006.01) | |
| F24F 11/75 | (2018.01) | |
| F24F 11/30 | (2018.01) | |
| F24F 11/77 | (2018.01) | |
| F24F 120/10 | (2018.01) | |

(52) U.S. Cl.
CPC ... *F24F 2003/1675* (2013.01); *F24F 2120/10* (2018.01); *F24F 2221/02* (2013.01)

(56) References Cited

U.S. PATENT DOCUMENTS

| | | |
|---|---|---|
| 7,186,371 B1 | 3/2007 | Watling |
| 7,674,440 B2 | 3/2010 | Martin |
| 8,551,399 B2 | 10/2013 | Shannon et al. |
| 9,938,724 B2 * | 4/2018 | Walters ................ E04F 13/074 |
| 2011/0097896 A1 | 4/2011 | Cursetjee et al. |
| 2014/0037496 A1 | 2/2014 | Pomeroy et al. |
| 2016/0038624 A1 * | 2/2016 | Krosney ............. B01D 53/007 |
| | | 422/121 |

OTHER PUBLICATIONS

Dimond, Valerie J. "Take over your makeover: Suite suite rennovation" from "Techning out your surgical suite", Healthcare Purchasing News, Apr. 2016, vol. 40 (4)., uploaded from http://mfphd.com/wp-content/uploads/2016/06/mfPHD-HPN-CoverStory-OR-SuiteRenovation0416.pdf on Jul. 17, 2016.

\* cited by examiner

HOSPITAL AND OPERATING ROOM DESIGNS AND STERILIZATION METHODS

BACKGROUND OF THE INVENTION

Field of the Invention

This invention is in the field of improved hospital and operating room designs and sterilization methods. These designs and methods are intended to reduce the microbial burden in these rooms, and thus the risk of Surgical Site Infections (SSI) and Hospital Acquired Infections (HAI).

Description of the Related Art

According to the Centers for Disease Control, in the US, there are approximately 1.8 million cases of Hospital Acquired Infections per year, and about 300,000 Surgical Site Infections a year. These infections are primarily caused by microorganisms (microbes) such as *staphylococcus aureus*, coagulase-negative staphylococci, *enterococcus* spp., *escherichia coli, pseudomonas aeruginosa, enterobacter* spp., *klebsiella pneumoniae, candida* spp., and other microbes. These infections result in a high rate of death and morbidity, and as well as a considerable amount of expense, and thus constitute a major medical problem. This problem is compounded because increasingly, these microorganisms are antibiotic resistant.

As a result, there has been a significant amount of interest in finding methods to reduce the number of microbes present in clinical areas, such as hospital operating rooms, emergency rooms, rooms for immunocompromised patients, and other clinical areas.

Some workers have focused on methods of delivering clean air to such areas. This includes the methods of Panelli (U.S. Pat. No. 6,132,309), Beaver (U.S. Pat. No. 7,125,332) and Curstejee (US 2011/0097986). Additionally, modern practice in this area commonly includes use of High-efficiency particulate arrestance (HEPA) filters, Ultra Violet (UV) sterilization techniques, and fixed airflow rates. Additionally, various regulatory codes and standards, such as requirements for a minimum number of air change rates per hour to maintain adequate ventilation, also are important in this area.

Other workers have focused on methods to provide vapors or other airborne disinfecting agents. Here Bioquell Inc., a UK company with US offices in Horsham Pa., has been active. Prior art by Bioquell includes Watling (U.S. Pat. No. 7,186,371), Martin (U.S. Pat. No. 7,674,440), and Pomeroy (US 2014/0037496). Other work in the field includes Shannon (U.S. Pat. No. 8,551,399).

Despite these and other efforts, the incidence of Hospital Acquired Infections and Surgical Site Infections remains unacceptably high. Thus further advances in the field are needed.

BRIEF SUMMARY OF THE INVENTION

The invention is based, in part, on the insight that microbes can exist on essentially each and every surface of a hospital or clinic treatment room, including hidden or obstructed services, and that the only way to assure that the microbial burden is consistently reduced is to employ airborne sterilizing agents that can penetrate to all surfaces of the hospital or clinic room.

The invention is also based, in part, on the insight that such airborne sterilizing agents are generally harmful to humans, and thus to be able to be used on a frequent basis, systems and methods must be devised to make the operation convenient, simple, safe, and nearly foolproof.

The invention is also based, in part, on the insight that even after an effective sterilizing cycle, microbes will again enter a room as soon as the room is opened to the outside, and humans again enter the room. Thus to reduce the risk of microbial borne infections, it is useful to employ air curtains of sterilized air (often HEPA and/or UV sterilized air), often best delivered by various types of laminar flow delivery devices. These laminar flow delivery devices should ideally be configured in a manner that is compatible with the use of the previously discussed airborne sterilizing agents.

In some embodiments, the invention may be a system and method of reducing the risk of microbial infections such as Hospital Acquired Infections (HAI). This system and method will typically rely upon rooms (chambers) equipped with airborne sterilizing agent generators, suitable occupancy and environmental sensors, control mechanisms, and electronic actuator regulated air control devices so as to allow, with very little operator effort, the same chamber to be both thoroughly treated with airborne sterilizing agents, and afterwards also provide suitable laminar flow sources of sterilized air.

In some embodiments, the invention may be a hospital or clinic chamber based system and method of reducing a risk of HAI. In a preferred embodiment, this will be an automated system and method that is controlled by one or more computer processors. This chamber will typically have a supply air (e.g. a damper-controlled outside air) intake that will take outside air and sterilize it (often by using a HEPA filter and/or UV sterilizer), as well as a damper-controlled air return. The chamber will typically distribute this sterilized outside air inside the chamber by using a ceiling mounted structural device (e.g. a load bearing structure, and a laminar air flow system (e.g. laminar array) mounted on the structural device), to blow HEPA filtered and UV sterilized supply air over a defined field in said chamber, thus providing an air curtain that helps protect against airborne microbes.

Note that although the ceiling mounted structural device performs multiple purposes, such as supporting the laminar array, providing support for hanging medical equipment, and other functions, typically the HEPA filters used to provide HEPA treated air will reside elsewhere, and the HEPA treated air will flow to the laminar array mounted on the ceiling mounted structural device though one or more air ducts, as is shown in FIGS. 3-6.

To sterilize the chamber, the invention will verify that no humans are present the chamber and then restrict access to the chamber. The invention will then isolate the interior air flow in the chamber from outside air (e.g. the hospital or clinic's main air supply) by closing at least one air return damper and at least one supply air damper. The invention will then activate an air phase anti-microbial agent generator, configured to fill the chamber with air phase anti-microbial agents at a time and dose level configured to kill at least a substantial majority of microbes in said chamber. Upon completion of this process, the invention will deactivate the generator, and set the dampers (e.g. at least opening the return damper and the at least one supply damper) and other air flow mechanisms to flush the remaining air phase anti-microbial agents from the chamber, often using a catalytic converter to deactivate any remaining air phase anti-microbial agents. In other embodiments, particularly when air duct access to the outside of the building is available, the air phase anti-microbial agents can be rapidly purged to the outside air. This latter option is particularly useful for emergency purge situations, and/or when a rapid stop of the sterilization process mid-cycle is desired.

Other suitable control mechanisms, devices, techniques and equipment to facilitate this process and other related useful processes will also be discussed.

DETAILED DESCRIPTION OF THE INVENTION

Nomenclature

Figure 1:
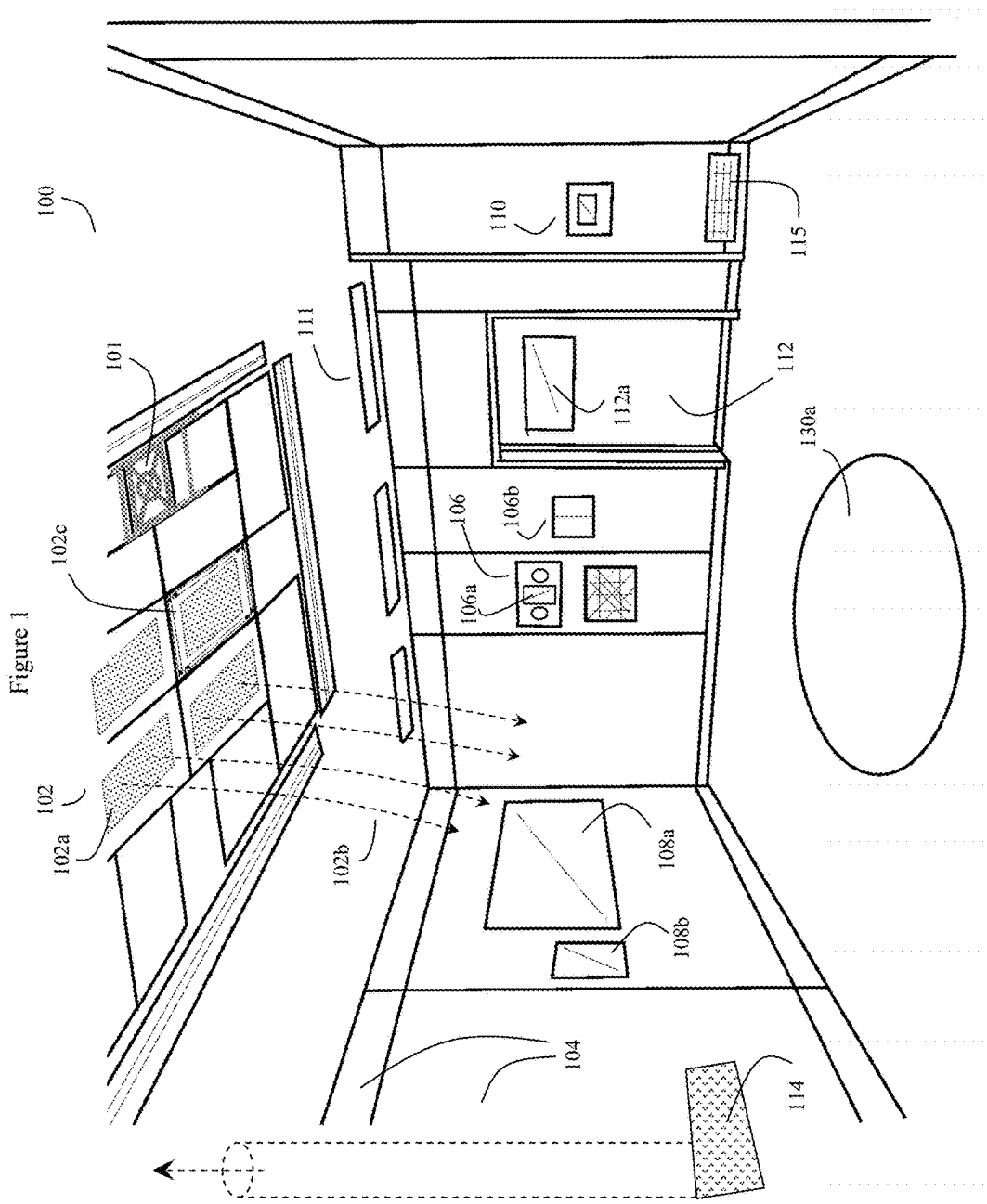
FIG. 1 shows an example of an operating room type chamber configured according to certain embodiments of the invention.

In this disclosure, the term "chamber" will often be used as a generic term for the room where the invention's systems and methods are being applied. Although hospital or clinic operating rooms are often used as specific examples for this type of room, these examples are not intended to be limiting. For example, the invention's systems and methods may also be applied to non-operating room hospital or clinic rooms, such as Intensive Care Units (ICU), and may be particularly useful where immunocompromised or infectious patients may be treated. The invention may also be useful for mobile clinics, field hospitals, combat support hospitals, and the like.

In this disclosure, the term "microbial" or "microbe" will be used to discuss bacteria, fungi, spores, viruses, and other microscopic pathogens, in particular microscopic pathogens associated with Hospital Acquired Infections (HAI) and Surgical Site Infections (SSI).

In this disclosure, the term "HAI" will be used as a generic term to discuss infections obtained from these microbial pathogens in a hospital or clinic setting, and SSI are considered to be a subset of HAI. Thus the term "HAI" encompasses "SSI".

In this disclosure, "damper" will often be used as a term for a valve or plate used to regulate the flow of air inside of a duct or other type of air handling device. Here unless otherwise specified, assume that the dampers are equipped with solenoids, motors, or other actuator mechanisms that allow the dampers to be opened or shut by a control mechanism, which may be a computerized control mechanism. Note that the term "valve" and "damper" are often used as alternate expressions for the same thing.

Use of computer actuated dampers, sensors, and other computer automated methods: A large percentage of clinic and hospital unfavorable events are caused by human error. Thus in a preferred embodiment of the invention, many of the devices and methods described herein may be computer controlled methods, used to reduce such human error related problems. However, unless explicitly claimed, use of computer control methods are not intended to be limiting. For example, in some embodiments, it may be necessary to operate the system in a fallback method under direct human control. In other embodiments, it may be useful to include the option of direct human control over certain equipment to allow for human supervision and interruption of certain sequences when, in the judgment of the human operators, such direct human control is necessary.

Turning to the invention: In some embodiments, the invention may be a system or method of reducing the risk of HAI (e.g. by reducing the microbial burden of a room used in patient care). This method relies, in part, on a combination of airborne antimicrobial agents to find and inactivate microbes on various surfaces and items in the room, and laminar air flow systems configured to use air curtains of sterilized air to help direct microbes away from patients.

Expressing the invention in methods terminology, the invention may comprise various devices and various steps, all working together as a system. To reduce the microbial burden of the room or chamber, the invention operates by verifying (often by automatic devices) that no humans are present in the chamber and then (again often by automatic devices) restricting access to this chamber prior to the commencement of sterilization.

Note that the chamber will preferably comprise air impermeable chamber walls, ceiling, and floor, although in some cases, walls or ceilings with limited porosity may also work so long as the porosity is limited enough as to constrain sterilizing agents inside the chamber, and to constrain the migration of microbes outside the chamber from migrating through the walls to inside the chamber. The walls of the chamber will typically be made of a material that is easy to clean, and that is not adversely affected by the sterilizing agents. Here materials such as glass and stainless steel, or other material able to withstand degradation by the sterilizing agent may be used.

Chambers intended for human occupancy typically provide air flow by providing a system by which outside air can enter into the chamber, and interior air inside the chamber can return to the outside air. Often this air flow is controlled by appropriate dampers. Here, the invention will typically operate by isolating (often by automatic devices), the interior air flow in the chamber from outside air by closing at least one return damper (typically actuator controlled) and at least one supply air damper (also typically actuator controlled).

For some clinical chambers, such as operating rooms, it is desirable to configure the chamber air supply so that the chamber obtains interior air from sterilized outside air. According to the invention, this sterilized outside air may be distributed inside the chamber using a laminar array (laminar air flow system) mounted or associated with a ceiling mounted structural device. This laminar array portion of the ceiling mounted structural device will typically comprise a load bearing structure, with a laminar air flow system mounted on the structural device. This laminar air flow system may be configured to blow sterile air (typically HEPA filtered and UV sterilized supply air) over at least a defined field in the chamber, often forming an air curtain around this defined field. For an operating room, this defined field may be the operating table. To control the supply of sterile outside air, in some embodiments this laminar air flow system will be connected to the at least one supply air damper (preferably also actuator controlled and often configured for automated operation).

For the sterilization cycle, the invention may operate by closing (often by automatic devices) at least one (actuator controlled) supply air damper, and activating (often by automatic devices) an air phase anti-microbial agent generator. This generator will typically be configured to fill the chamber with air phase anti-microbial agents, such as a hydrogen peroxide vapor or mist, and to keep the levels of these agents elevated for a time and dose level configured to kill at least a substantial majority of the chamber's microbes. The invention may also monitor the environment inside the chamber, and adjust other parameters, such as temperature and humidity, so that the sterilizing agent acts in a consistent and predictable manner.

Following this microbial reduction cycle, the invention will then typically (often by automatic devices) deactivate (e.g. turn off) the generator, and flush (again often by automatic devices) any remaining air phase anti-microbial agents from the chamber by, for example, at least opening the (actuator controlled) return damper and opening the at least one (actuator controlled) supply damper. Fans may also be activated as appropriate. This acts to flush the air phase antimicrobial agents from the chamber.

When viewed from the operating room standpoint, the net result is to obtain an operating room with an unusually low microbial burden, and configured, even after the sterilization cycle, to keep the microbial burden low over at least certain defined fields or regions of the chamber (e.g. over the operating table) by providing laminar flow sources of sterile air that, for example, may provide an air curtain against any airborne microbes carried by dust particles or droplets entering these regions or fields.

Figure 2:
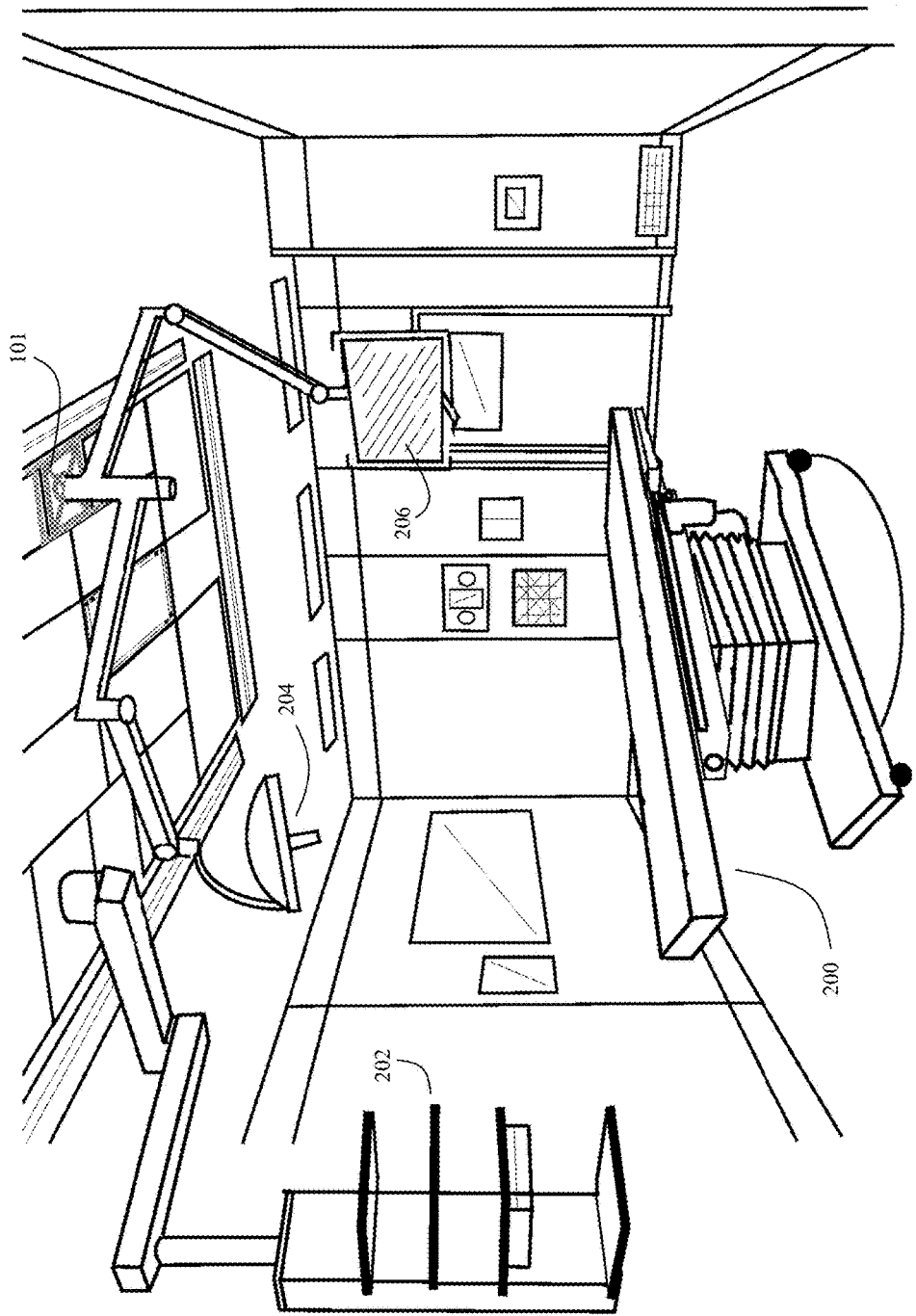
FIG. 2 shows an embodiment of the operating room or chamber configured with an operating table and various types of boom mounted operating room equipment.

FIGS. 1 and 2 show an example of such an operating room type chamber (100) configured according to certain embodiments of the invention. On the ceiling, the invention's ceiling mounted structural device (101) can be mounted. In addition to accommodating an array of laminar air flow devices and other utilities such as lighting, this structural device (101) can support a modular grid system with a load bearing structure configured to accommodate multiple types of ceiling mounted devices with various weights (loads) and dimensional tolerances. This structural device (modular structural grid) (101) may thus support the ceiling (e.g. provide an apparent ceiling to inside observers), the laminar array, medical equipment, as well as access to various hospital or clinic utilities (e.g. power, medical gas, etc.) as desired.

Figure 7A:
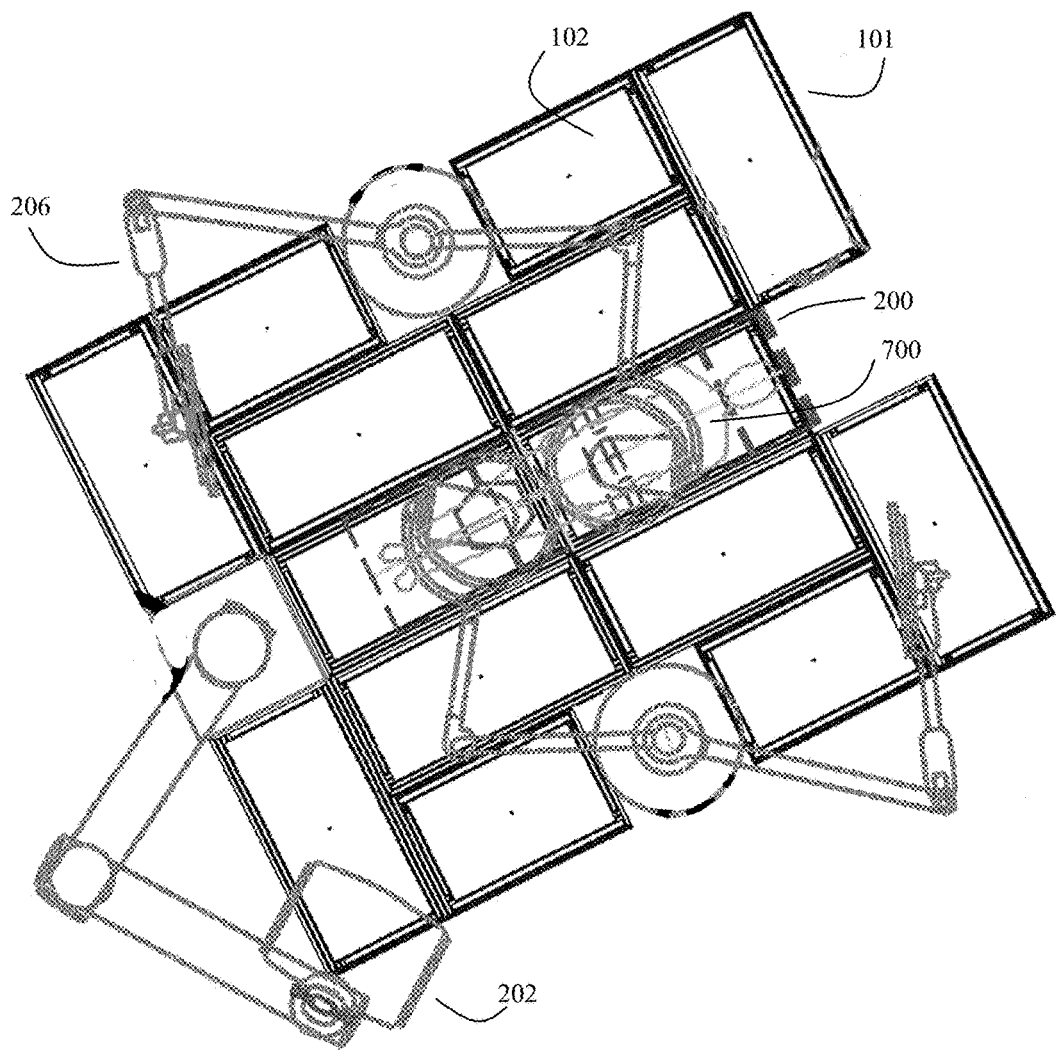
FIG. 7A shows a top down view of a portion of an operating room type chamber as seen from the perspective of a viewer positioned above the invention's ceiling mounted structural device.
Figure 7B:
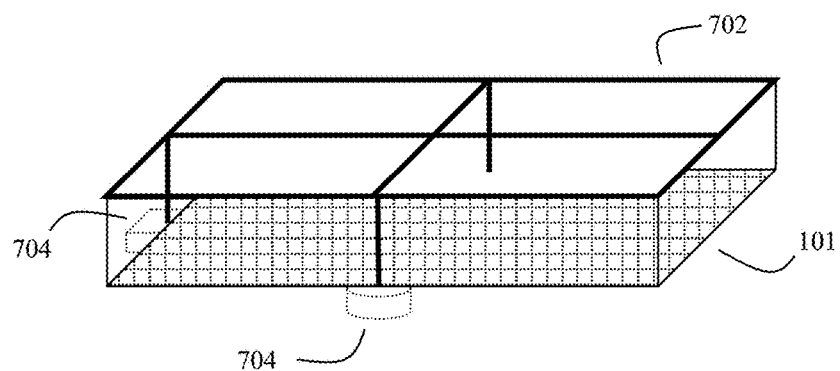
FIG. 7B shows a detail of how the ceiling mounted structural device may be mounted in the ceiling of an operating room.

In some embodiments, it may be useful to use a prefabricated structural system, such as a system of powder coated structural steel grids, to form a plurality of internal grids configured to provide underlying support for the array of laminar flow devices, medical equipment, and utilities held by structural device (101), see also FIG. 7B (702).

In some embodiments, which may be particularly useful when the chamber is an operating room and the defined field in the chamber is an operating table, the ceiling mounted structural device may have a generally polygonal shape, such as a rectangular shape, or a more complex shape formed from a plurality of rectangles. This ceiling mounted structural device may be further configured with a plurality of internal grids. In a preferred embodiment, at least some of these grids may be configured to accommodate electrical conduits, preferably larger conduits with diameters of around 2 inches for maximum compatibility with a broad range of additional equipment, such as equipment useful for Operating Room (OR) purposes. At least some of these grids or other grids may be configured to supply structural support for additional equipment, such as for standard operating room utility pendants/booms, surgical lights, and other boom-mounted equipment. This is shown in more detail in FIG. 2. See also FIGS. 7A-8B.

The ceiling mounted structural device (101) will also typically have various mounted laminar air flow systems (102), which will introduce clean HEPA filtered (and often UV sterilized) supply air into the operating room, often through perforations in the overhead lighting fixtures (102a) (perforated panels). This laminar air flow system (102) will often be designed so as to produce a perimeter air curtain (102b) over a defined field of the operating room, such as in the region (130a) where an operating table may be placed. Here the lighting system may incorporate integrated lighting, such as integrated light emitting diode (LED) lighting. This lighting may be disposed in a perimeter (102c) around the perforated panels (102a), or in other locations.

Put alternatively, this laminar air flow system may, in a preferred embodiment, further comprise a plurality of air curtains that produce a plurality of directionally-controlled airstreams (102b). This is often referred to in the alternative as a "laminar array". These airstreams are configured to reduce penetration of particles from area outside of the operating table to an area inside the operating table.

As previously discussed, the walls of the chamber (104) will often comprise materials selected to be easy to clean and sterilize, and resistant to any deterioration caused by air-phase anti-microbial agents such as hydrogen peroxide ($H_2O_2$). These materials can comprise medical grade glass (or glass-like material), stainless steel, or other easy to clean materials that are resistant to deterioration caused by the airborne sterilizing agent(s).

The walls (104) may or may not have illumination or customized backgrounds. In some embodiments, it may even be useful to put computer controlled display screens behind transparent walls so that the appearance of the operating room can be customized according to the needs at hand. The wall displays may, for example, be configured to a pleasant and reassuring display to show patients upon entry. The wall displays can then reconfigured during an operation, as desired, to show images containing medical information, thus making it easy for physicians to request additional data in an easy to see format as desired.

In some embodiments, at least the substantial majority (e.g. greater than 50% and often greater than 90%) of the chamber's walls may be covered with materials, such as glass or stainless steel, selected to be resistant to the particular air phase anti-microbial agents that are being used.

The system will also comprise an air phase antimicrobial agent generator (106), such as a hydrogen peroxide vaporizer/fogger/aerosol generating unit shown here as a particular example. This generator may operate according to methods of Pomeroy (US 2014/0037496), Watling (U.S. Pat. No. 7,186,371), Shannon (U.S. Pat. No. 8,551,399) or other methods. This generator (106) may further comprise a control touchscreen (106a), such as a hydrogen peroxide fogging control touchscreen, and containers of the antimicrobial agent (106b), such as modules configured to hold bottles of hydrogen peroxide.

In some embodiments, the generator may operate by converting an aqueous solution of hydrogen peroxide into air phase hydrogen peroxide by using any of a misting, nebulizer based, vaporizing based, or aerosol generating type process.

Some air-phase antimicrobial agents, such as hydrogen peroxide, require that the room humidity and/or temperature be controlled in order to achieve maximum anti-microbial effectiveness. Thus in some embodiments, the air phase anti-microbial agent generator may be a combination generator and humidifier that also operates by regulating humidity, or alternatively the chamber may contain humidity and/or temperature sensors and regulating equipment that operates independently of the generator.

In some embodiments, the system will also comprise one or more medical grade touch-workstations (108a, 108b) for medical information, medical images, and other digital media. This workstation may optionally be integrated into the glass walls (104) of the chamber for greater sterility and to protect the workstation electronics. Other touch panels may also be provided for other functions, such as controlling other room lighting (111).

In a preferred embodiment, the invention will further comprise at least one computer processor, which will be configured to control many or all of the invention's various steps. In these embodiments, for example, this (at least one) computer processor may be used (often in conjunction with various occupancy sensors). Prior to the start of a sterilization cycle, this computer processor may use the occupancy sensors to first verify that no humans are present in the chamber and then to restrict access to the chamber (e.g. by automatically locking doors) so that outsiders cannot accidentally enter. Various safety overrides can, of course, also be incorporated into the system.

In some embodiments, this at least one computer processor may also be used to isolate interior air flow in the chamber from outside air by closing at least one computer controlled return damper and at least one computer controlled supply air damper (here assume that the chamber is configured to return interior air from inside the chamber to the outside using this at least one computer controlled return air damper). See FIG. 4 for more detail.

In some embodiments, the laminar air flow system may also be connected to at least one computer controlled supply air damper, and the system's (at least one computer processor) may be used to activate the air phase anti-microbial agent generator (106).

In these embodiments, at the end of a sterilizing cycle, the system's (at least one) computer processor may also be used to deactivate this anti-microbial agent generator (106), and to flush any remaining air phase anti-microbial agents from the chamber by opening the computer controlled return damper and the (at least one) computer controlled supply damper. These steps are shown in more detail in FIGS. 3-6.

In some embodiments, this (at least one) computer processor may be controlled and monitored by using at least one touch panel equipped graphical user interface terminal. This terminal may be mounted either on an interior chamber wall (110) or exterior to the chamber, or in both places. FIG. 1 shows an example of this type of computer processor control unit (110), which optionally may also be integrated or embedded into or behind the glass walls (104) of the chamber. These control units will often include a master system control-touch panel. This can be used for controlling at least portions of the sterilization process, sterilization safety systems (e.g. door locks, sensors), and the like. This or an alternative control panel may also be used to control other aspects of the chamber's environment, such as lighting, air conditioning, and the like. To prevent accidental misuse, it may be preferable to separate the sterilization control panel from the control panel used to implement more standard aspects of the chamber, such as lighting.

The chamber (100) will also typically comprise at least one door (112) or door system. This door system will typically be configured to hermetically seal when shut, and also will be configured with locks, such as computer controlled locks. For safety purposes, these computer controlled locks will usually have a manual override. For safety purposes, the door will also usually have one or more windows (112a) so that outside observers can visually confirm the occupancy status of the room. If exterior sterilization control panels are used, it may be desirable to locate these control panels so that anyone using the control panel can look through a window and see what is happening. Alternatively, an outside control panel can also incorporate video displays of the inside of the chamber. Again, the idea is to make sure that no one is present in the chamber before sterilization begins.

In a preferred embodiment, the chamber (100) will be equipped with at least one-way computer operated door locks. Here, using the at least one computer processor to restrict access to the chamber can (for example) comprise setting these at least one-way computer door locks to restrict humans outside the chamber from entering into the chamber. For safety reasons, it would be useful to configure the locks so that any humans inadvertently left inside the chamber can manually exit even after sterilization starts. It may also be useful to configure the doors with manual "open" overrides on the outside as well.

Other methods of ensuring that no humans are present in the chamber (100) during a sterilization cycle can also be used. For example, the at least one computer processor can be used to monitor at least one occupancy sensor (see FIG. 4, 400), and preferably a plurality of different occupancy sensors, to reduce the chances of error. These occupancy sensors may include one or more motion sensors, infrared sensors, video cameras, carbon dioxide sensors, sound sensors, and the like.

Figure 5:
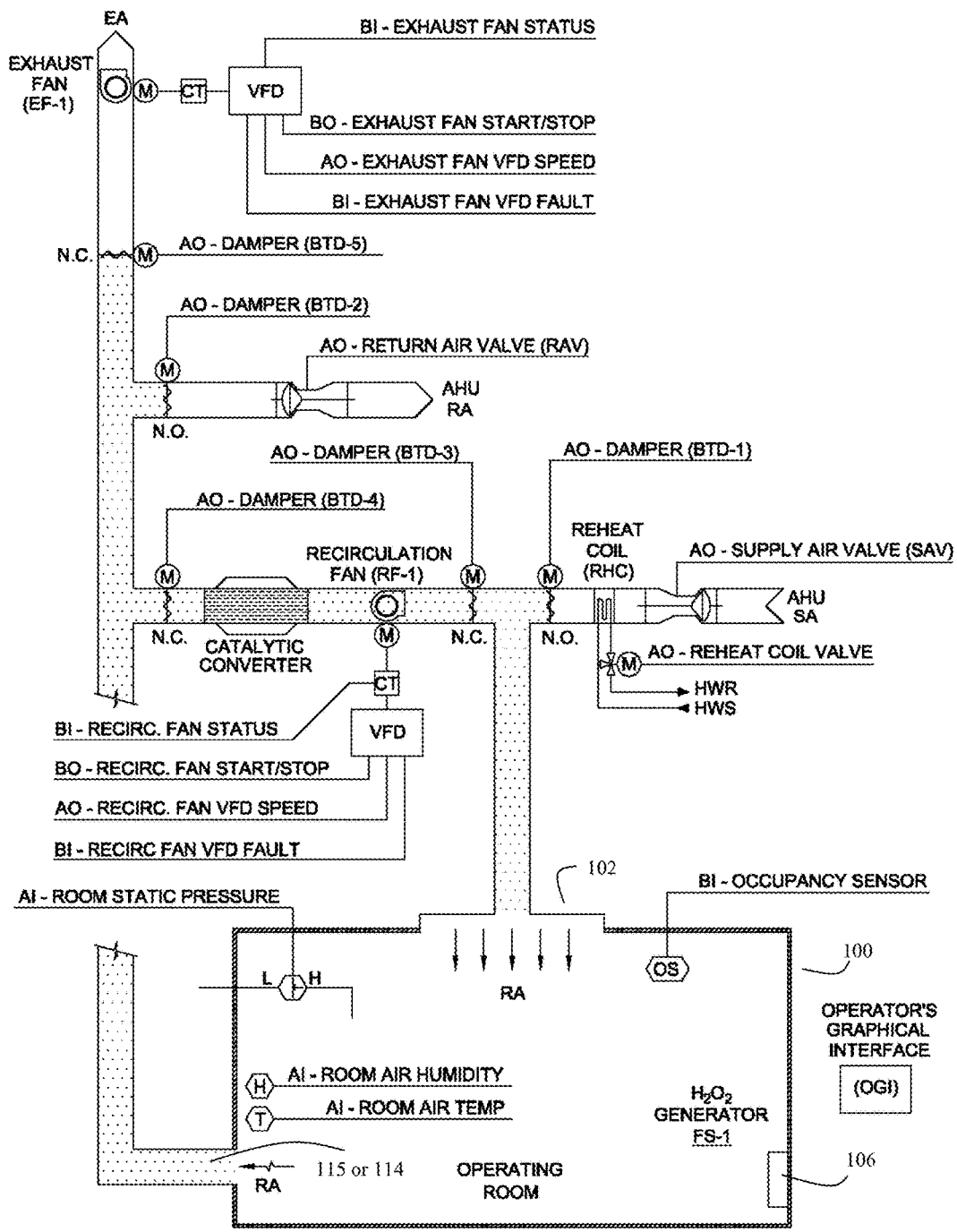
FIG. 5 how the invention may operate during a normal termination of a sterilization cycle.
Figure 6:
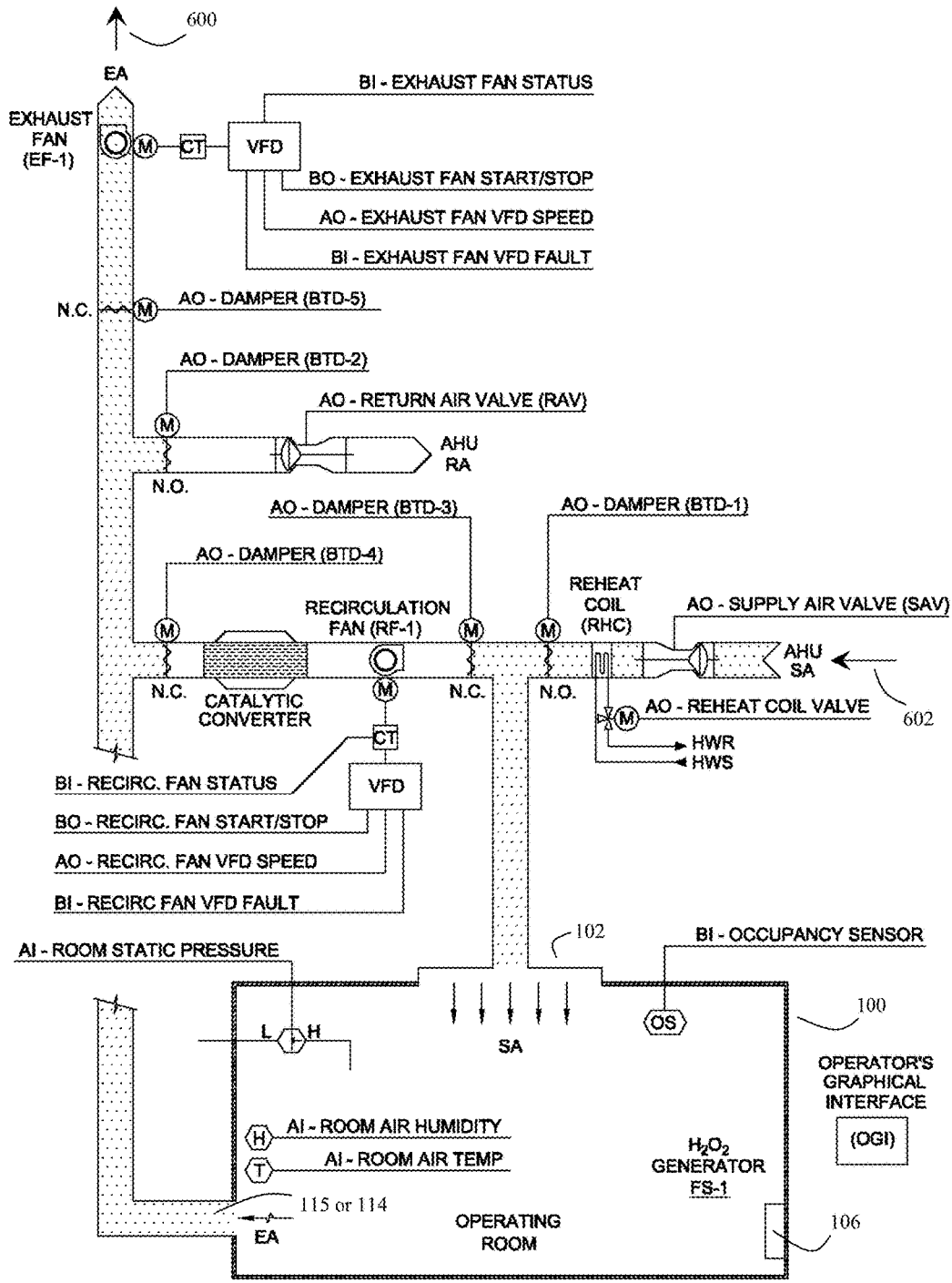
FIG. 6 how the invention may operate during an accelerated or "emergency purge" termination of a sterilization cycle.

After the sterilization cycle has commenced, before the chamber/room can be occupied again, residual air phase antimicrobial agents must be removed from the chamber (100). Here there are at least two ways to do this. One way, illustrated by FIG. 5, is to run the air though a built-in catalytic extraction unit that destroys all remaining antimicrobial agents. An alternative way, illustrated by FIG. 6, is to exhaust the antimicrobial agents into the outside atmosphere. These options can be selected based on available facilities and time available to complete the sterilization cycle. The rapid exhaust option can also be utilized if an emergency purge is required, and thus is sometimes referred to in the alternative as the "emergency" option.

As shown in more detail in FIG. 5, to remove air phase antimicrobial agents after the sterilization cycle, the chamber will also typically comprise a catalytic extraction unit comprising a room air intake, at least one fan, at least one a computer controlled catalyst damper, and a catalyst (catalytic converter) to deactivate any remaining air-phase anti-microbial units. The air intake to this catalytic extraction unit is shown as (114). In some embodiments, this catalytic extraction unit can also be used as an emergency purge loop while in other embodiments (see FIG. 6), during emergency operation, for higher exhaust rates, the catalytic portions may be temporarily bypassed.

In the catalytic removal cycle, as shown in FIG. 5, the system may use at least one computer processor to turn on at least one fan to further flush remaining air phase anti-microbial agents from the chamber. The system may additionally, or alternatively, use at least one computer controlled catalyst damper and a catalyst (catalytic converter) to deactivate any remaining air-phase anti-microbial agents.

The catalyst will typically act to degrade the air phase anti-microbial agents into harmless molecules. For example, if the air-phase antimicrobial agents are hydrogen peroxide ($H_2O_2$), then the catalyst may degrade these agents into harmless molecules such as water ($H_2O$) and oxygen ($O_2$).

As previously discussed, in some embodiments, the chamber (100) may be further equipped with at least one anti-microbial agent sensor configured to monitor the levels, concentrations, or amounts of the air-phase anti-microbial agents present in the chamber air. In at least computer control versions of the invention, this at least one anti-microbial agent sensor can further be configured to transmit data to the at least one processor used to control the system. In a preferred embodiment, this at least one processor may be configured to set the at least one-way computer door locks and door (112) so that the door only allows humans to enter the chamber after the anti-microbial agent sensor(s) report that the air phase anti-microbial agents are at a non-toxic level.

During conventional operation when the chamber is not going through a sterilization process, a more conventional air return (115) may be used.

FIG. 2 shows an embodiment of operating room or chamber (100), here configured with an operating table (200) and various boom mounted operating room equipment e.g. (shelves 202, lights 204, monitor 206) mounted on booms that are supported by the ceiling mounted structural device (101).

Figure 3:
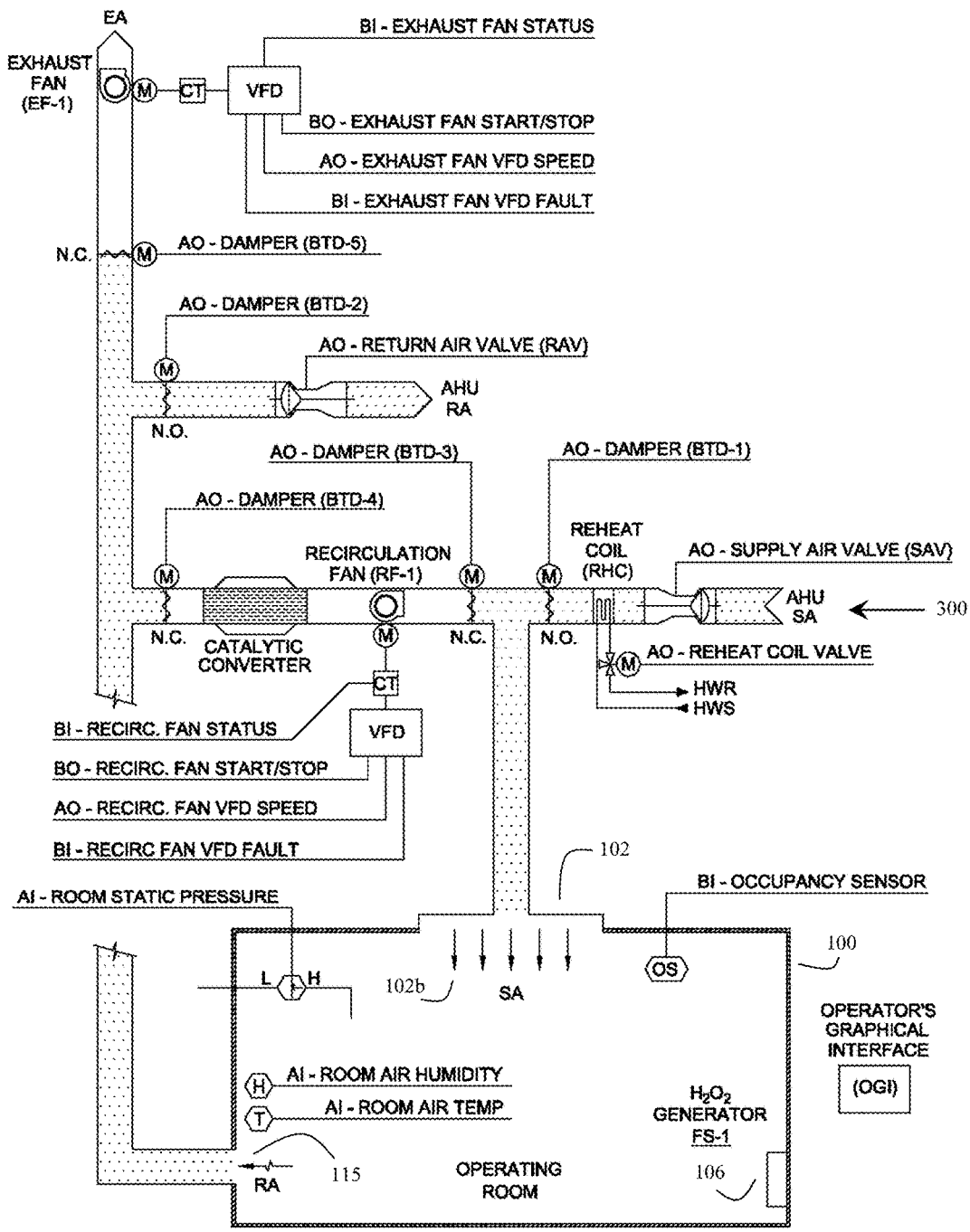
FIG. 3 shows how the invention may operate between cycles of sterilization.

FIG. 3 shows an embodiment showing how the invention's chamber sterilization equipment may act during normal operation, such as in between sterilization cycles, when the room may be occupied by physicians, patients, and other humans. Note that as previously discussed, the system contains many computer connected and controlled air dampers (dampers), fans, and drivers that may, for example, be controlled by at least one computer processor. This at least one computer processor may form part of control unit (110), or may form part of another control unit as desired.

In FIGS. 3-6, the various terms are defined in Table 1 as follows:

TABLE 1

| Abbreviation | Meaning |
|---|---|
| AO | Analog Output (e.g. 0-10 volts) |
| AT | Analog Input (e.g. 0-10 volts) |
| BO | Binary Output (e.g. 24 volts) |
| BI | Binary Input (e.g. 24 volts) |
| BTD-X | Bubble Tight Tamper |
| EF-X | Exhaust Fan |
| N.O. | Normally Open |
| N.O. | Normally Closed |
| RF-X | Recirculation Fan |
| RHC | Reheat Coil |
| RA | Return Air |
| RAV | Return Air Valve |
| SA | Supply Air |
| SAV | Supply Air Valve |
| VFD | Variable Frequency Drive |
| SA | Supply Air |
| AHU | Air Handling Unit |

In normal operation, most of the system is shut down. Clean HEPA filtered air (300) enters through the supply air valve (SAV) in an open configuration, is optionally heated or reheated, and passes through normally open damper (air valve) BTD-1. (Here the term "bubble tight damper" or BTD denotes that the damper or air valve, when shut, closes tightly enough that when fluid is applied to test for sealing efficiencies, no bubbles can be found.)

The air passes through various optional HEPA filters and/or UV sterilizers (not shown) and will typically enter the chamber through the various mounted laminar air flow systems (102, 102a) previously shown in FIG. 1, and may form air curtains (102b) as desired. Return air exits the chamber via an air return, such as FIG. 1 (115). This return air is directed outside the chamber via normally open damper (air valve) BTD-2 and through the return air valve (RAV). This process may be assisted by various fans, as desired (not shown).

Figure 4:
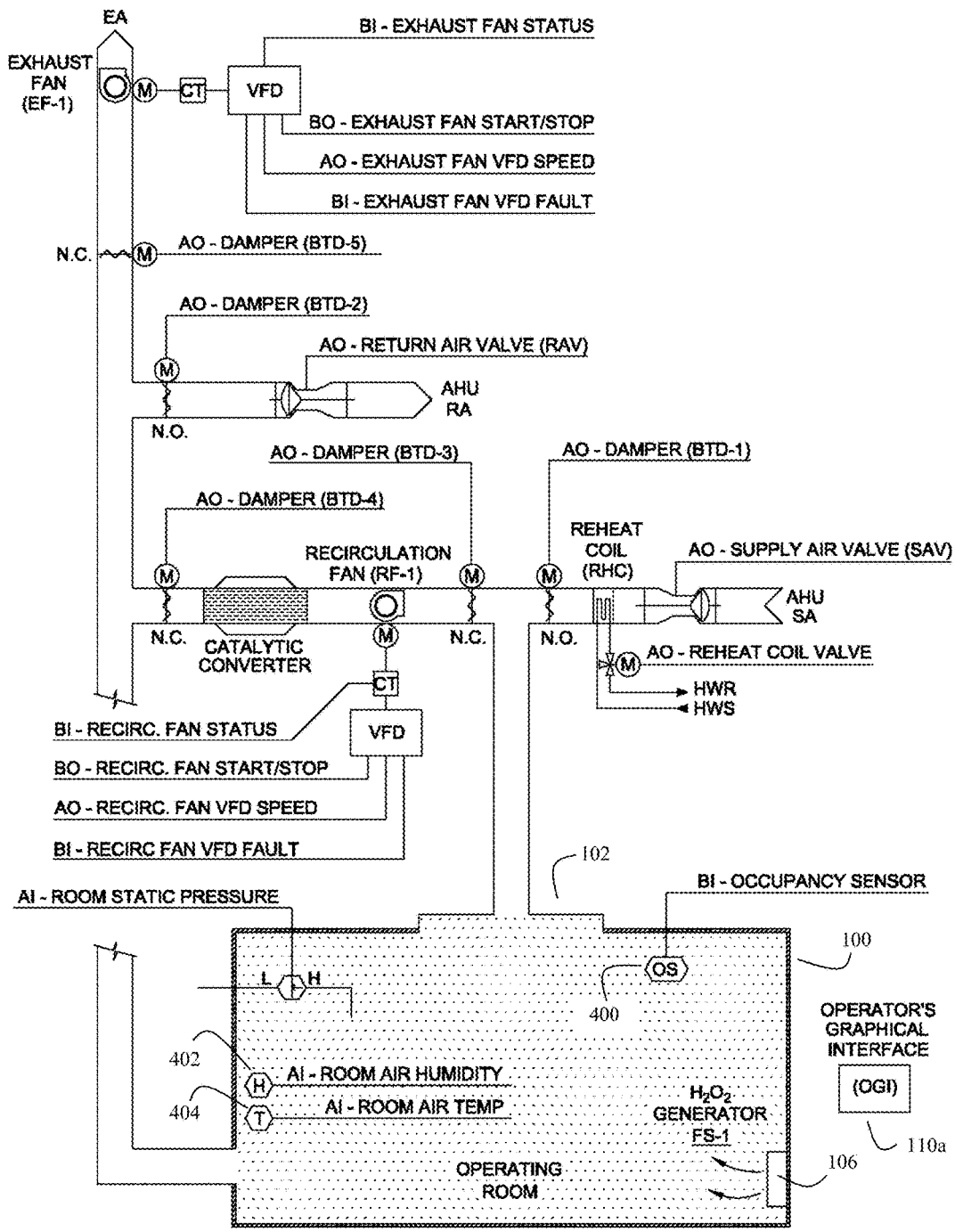
FIG. 4 shows how the invention may operate during the initiation of a sterilization cycle.

FIG. 4 shows an embodiment of how the system may operate during a sterilization cycle. As previously discussed, to insure safety, before moving to this phase of the cycle, the system's computer processor will normally check the status of at least one occupancy sensor (400), and preferably a plurality of occupancy sensors operating by more than one detection modality, before initiating this sterilization cycle. This process may be controlled by suitable touch panel mounted graphical interface terminals mounted either inside the chamber (e.g. on an interior chamber wall, such as 110), or outside the chamber (e.g. 110a), or in both places.

Immediately before the sterilization phase, the computer processor, after verifying that the chamber (100) is empty, will then restrict access to the chamber by, for example, automatically locking door (112).

Often before the sterilization processes commences, the computer processor may monitor and adjust the room air humidity and temperature using appropriate sensors (402, 404), and optionally also monitor and adjust room static pressure as well, to optimize the integrity of the sterilization process.

During the sterilization phase, the computer directs normally open air valve (damper) BTD-1 to shut, and there is no air entering the room through the laminar flow system (102). The air phase anti-microbial agent generator (106) is turned on, flooding the chamber (100) with an air born sterilizing agents such as hydrogen peroxide vapor or mist. Normally open air valve or damper (BTD-2) is also computer directed to be shut, and normally closed dampers BTD-4 and BTD-5 are also directed to remain shut.

So the sterilizing agent remains trapped in chamber (100), where it will sterilize the room and its various contents. During the sterilization process, in some embodiments, the computer processor may continue to monitor and adjust the room air humidity and temperature using appropriate sensors (402, 404), and optionally also monitor and adjust room static pressure as well, to help further ensure the integrity of the sterilization process. Other sensors may also be used to monitor levels of air-phase anti-microbial agents as well.

FIG. 5 shows how after sterilization, room (chamber) air may be exhausted through a catalytic system in order to remove any remaining sterilizing agent, and to once again make the room suitable for occupancy. The air phase anti-microbial agent generator (106) will be turned off, either by the system's computer processor, exhaustion of anti-microbial agents, or other method. The room air, which contains the air-phase antimicrobial agent, exits the room through the appropriate return air register (114 or 115). The computer closes normally open air valve (damper) BTD-2, and keeps normally closed air valve (dampers) BTD-5 and BTD-1 closed as well. The computer opens normally closed air valve (damper) BTD-4 and BTD-3, and turns on recirculation fan RF-1. As a result, air, containing the anti-microbial agents (e.g. hydrogen peroxide) passes through catalytic converter (500), where the antimicrobial agents are destroyed. The air, now free of any antimicrobial agents, reenters room (100) through the laminar air flow systems (102). This recirculation process can continue until the computer (usually assisted by various sensors and timers) determines that the level of remaining anti-microbial agents has now dropped to an acceptable level. Usually, the computer system will keep door (112) automatically locked until this time.

The one drawback of this catalytic recirculation method, however, is that it may take some time to operate.

FIG. 6 shows an alternate Emergency purge/Rapid exhaust process method of quickly removing anti-microbial agents from chamber (100). Here, as before, the system turns off the air phase antimicrobial agent generator (106). However the system bypasses the catalytic converter and recirculation system. Instead, the computer opens normally closed air valve (damper) BTD-5, and activates exhaust fan EF-1. The normally open damper BTD-2 is closed, and the normally closed damper BTD-4 continues to remain closed. Thus the chamber air, with its anti-microbial agents, may be directed outside the building via EA (600).

During this Emergency purge/Rapid exhaust process, the system directs normally open air valve (damper) BTD-1 to remain open. Thus clean HEPA filtered supply air (602) passes though the supply air valve (SAV), is optionally heated or reheated as desired, and this clean air, free of anti-microbial agents, enters the room through the laminar air flow systems (102).

An example of a sequence of operations, such as one that might be used by the system's at least one computer processor, and as also discussed in FIGS. 3-6, is shown below:

1.0 Standard (Surgery/Treatment) Operation:
All operations shall be controlled by an operating room specific controller and shall have full BacNet interface with the facilities Building Automation System (BAS). Each Operating Room (100) will have an Operator's Graphical Interface (OGI, 110, 110*a*). All set points and adjustments can be made at the OGI or at the facilities BAS.
A. Supply Air Valve (SAV) shall modulate in conjunction with Return Air Valve (RAV) to maintain a constant air flow of 25 Air Changes per Hour (ACH) and maintain the operating room at a positive pressure to surrounding spaces. The operating room shall be maintained at +0.05 inwg. Status of the HVAC system airflow and pressure relationships shall be fully integrated and indicated on the OGI.
B. Operating room space temperature shall be maintained +72 F (adjustable) by modulating the flow of heating water to a reheat coil.
C. Operating room space humidity will be maintained at 50% RH (adjustable) by regulating output of a localized humidifier. If humidity control is provided at the base building air handling unit, the OGI shall monitor and report the space humidity condition.
D. General space lighting will be provided by full dimmable LED lighting fully integrated to the OGI. Lighting shall be able to change color to indicate operational status of the operating room.

2.0 Room Sterilization Operation:
All operations shall be controlled by an operating room specific controller (e.g. computer processor) and shall optionally have full BacNet interface with a facilities Building Automation System (BAS). Each Operating Room will have an Operator's Graphical Interface (OGI) (e.g. 110, 110*a*). All set points and adjustments can be made at the OGI, Hydrogen Peroxide generator (106) or at the facilities BAS. (Note, BACnet is a communications protocol for building automation and control networks, and is now exemplified by ISO standard 16484-5.)
A. Room sterilization operation shall be initiated by a time of day command or from a manual operator's command from the OGI. Manual override of a time of day start will be made at the OGI prior to the start of sterilization sequence of operation.
B. Upon initialization of the sterilization sequence the room (100) shall be confirmed to be unoccupied by at least one local occupancy sensor (400) within the operation room. Upon verification of zero occupancy a countdown timer shall indicated the sterilization cycle is ready to begin. The OGI shall indicate the room is vacant of occupants and ready for sterilization.
C. Following confirmation of the unoccupied room the operating room doors (112) shall close and lock and the OGI shall indicate confirm the status of the doors. This status shall be confirmed by end switches on the door slides as well as the electro lock (door lock). Red LED lighting integral to the space shall be illuminated to indicate the room is not safe for inhabitants. Manual kill switches/Door releases shall be located adjacent to all points of egress within the room. Upon activation of a Kill Switch/Door release the system will require an operator resent at the OGI.
D. Upon confirmation and indication of the operating room doors (112) being closed and locked, the operating room shall be isolated from the main building air handling units by closing bubble tight control dampers (BTD). The SAV and RAV shall close in conjunction with dampers BTD-1 and BTD-2. The heating water valve on the operating room reheat coil shall be closed and the humidifier shall cycle off for the duration of the sterilization sequence. The status off the dampers shall be indicated on the OGI.
E. Upon confirmation of room isolation from the building air handling units, the sequence shall pause for a minimum of 300 seconds (adjustable) to assure the room is air is calm and all directional movement and turbulence has ceased. The status of the operation shall be indicated on the OGI.

F. Following the suspension of air turbulence, the room sterilization system (106) shall activate the hydrogen peroxide generator. The hydrogen peroxide generator shall sterilize the room based upon the onboard control systems. All status changes and actions shall be monitored at the OGI and the building automation system.

G. The hydrogen peroxide agent shall remain in the room until such time the generators onboard controls determine the room saturation has been achieved and the agent is ready to be evacuated.

H. Upon completion of the sterilization and dwell time the bubble tight dampers BTD-1 and BTD-2 isolating the catalytic convertor shall open. Upon confirmation of the dampers being fully open recirculation fan RC-1 shall activate drawing the operating room air and sterilization agent through the catalytic convertor. RC-1 shall run for a minimum of 360 seconds (adjustable) or until the rooms internal sensor indicates no sterilization agent remaining within the operating room. If a catalytic device is not incorporated within the design BTD-4 shall open and an operating room exhaust fan EF-1 shall activate to exhaust the agent. Upon confirmation of EF-1 start, BTD-1 shall open and SAV shall return to its normal operating condition to provide make-up air for the evacuation process. The evacuation process shall continue until the onboard controls on the hydrogen peroxide generator indicate the room is free of the agent.

I. Upon completion of the sterilization process, RC-1 shall deactivate and BTD-3 and BTD-4 shall close. Upon confirmation of closure of BTD-3 and BTD-4, BTD-1 and BTD-2 shall open. Upon confirmation of the open status of BTD-1 and BTD-2, SAV and RAV shall resume standard operation. The heating water reheat coil and humidifier shall be reactivated and shall operate in sequence until the operating room returns to its original adjustable set points. All activity and status shall be controlled and indicated at the OGI.

J. Upon confirmation status of the operating conditions of SAV and RAV, the door interlock shall be released and the red sterilization light shall return to the normal operation conditions. OGI shall indicate the OR is safe for occupancy and is ready for use.

FIG. 7A shows a top down view of a portion of the operating room (100) as seen from the perspective a viewer positioned above the ceiling mounted structural device (101). In the drawing, the observer is looking past the various laminar air flow systems (102) as if they were transparent or semi-transparent. The observer is also looking past various types of boom mounted equipment (e.g. monitors 206, shelves 202, lamps, etc.) and onto the top of an operating table (200) with a patient (700).

In a preferred embodiment, the operating table will be aligned with the orientation of the ceiling mounted structural device (101) and the various laminar air flow systems (102) so as to create an air curtain (FIG. 1, 102b) that sweeps the operating field clear of potentially microbe containing airborne particles.

Note that in some embodiments, as shown in FIG. 7A, the exterior dimensions of the polygonal shape of the ceiling mounted structural device (101) may exceed the exterior dimensions of the operating table (200). In some embodiments, this polygonal shape may be a rectangular polygonal shape (or at least may be composed of a plurality of rectangular polygonal shapes). The various laminar flow devices on the ceiling mounted structural device may be configured to produce a plurality of air curtains that may, for example, extend on all sides of a perimeter of the rectangular polygonal shape.

Ideally the ceiling mounted structural device and its various laminar air flow devices (e.g. laminar array) may be configured so that this air curtain perimeter will exceed the exterior dimensions of the operating table (200). This configuration will help further isolate the operating table (200) and the patient (700) from microbes borne on airborne particles originating from outside of the operating table.

As shown in FIG. 1, and elsewhere such as FIGS. 7A, and 8A-9C, in some embodiments, this laminar air flow system may be disposed on one or more interior structures within the rectangular shape of the ceiling mounted structural device (101). These laminar air flow systems may introduce an air flow configured to flush airborne particles from the area of the operating table (200) to an area outside of the operating table.

As previously discussed, for ease of construction, and compatibility with different types of equipment, at least some of the internal grids in the ceiling mounted structural device may be configured to accommodate electrical conduits with widths of at least 2 inches. Further, at least some of the internal grids may comprise weigh supporting members, some of which may be further equipped with flanges or other mechanical supports configured to supply structural support for standard operating room boom mounted equipment. See FIG. 7B for more examples.

FIG. 7B shows a detail of how the ceiling mounted structural device (101) may be mounted in the room. Here the ceiling mounted structural device (101) may either be a "false ceiling" that is mounted to structural support on the "real ceiling", or alternatively the ceiling mounted structural device may be suspended using modular support framing (702) or other type framing to various types of building structural supports (not shown). This modular support framing (702) may also be used to provide mechanical support for heavy boom mounted equipment (704) such as (202, 204, 206 etc.). This type of heavy boom mounted equipment is shown in Table 2 below.

TABLE 2

Boom and Lighting mount size (inches), weights & moments

| Vendor name | Mounting plate | Soffit | Weight/Moment |
|---|---|---|---|
| Stryker/Berchtold | T 23.5 × 23.5 | 25.5 × 25.5 | 2000 lbs/8020 ft lbs |
|  | S 15 × 15 | 23 × 23 | 1000 lbs/4020 ft lbs |
| Skytron | 17.5 × 17.5 | 24 × 24 | 1028 lbs/5606 ft lbs |
| Maquet | 20 × 20 | 25.59 round | 891-959 lbs/5962 ft lbs |
| Steris | TB 28 × 28 | 24 × 24 | 1987/11341 |
|  | TL 28 × 28 | 24 × 24 | 1732/8262 |
| Modular | 21 × 21 | 23 round | 1000 lbs/4010 ft lbs |

Figure 8A:
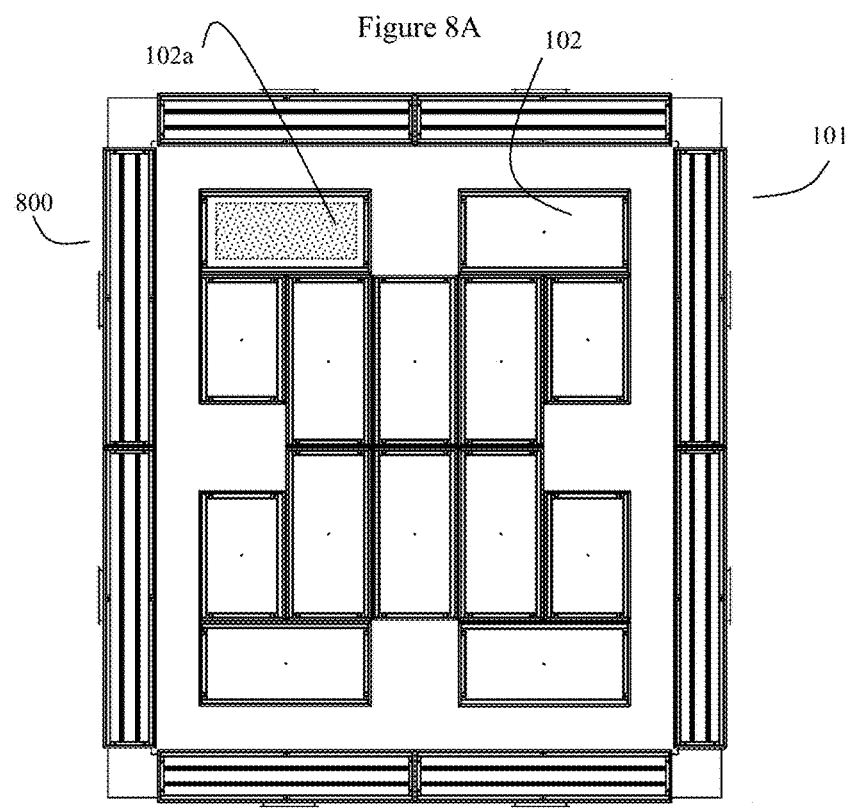
FIG. 8A shows an alternate view of the laminar array portion of the ceiling mounted structural device, here equipped with some additional perimeter lights and perimeter conduit paths.

FIG. 8A shows an alternate view of the laminar array portion mounted on the ceiling mounted structural device (101), here equipped with some additional perimeter lights (800) and perimeter conduit paths. Here assume that all of the mounted laminar air flow systems (102) are equipped with perforated panels (e.g. a perforated panel facing the room) (102a) so that air can flow gently into the room through a series of small openings (perforations). Examples of such perforated panels include the laminar flow diffusers produced by Krueger-HVAC, and other sources.

Figure 8B:
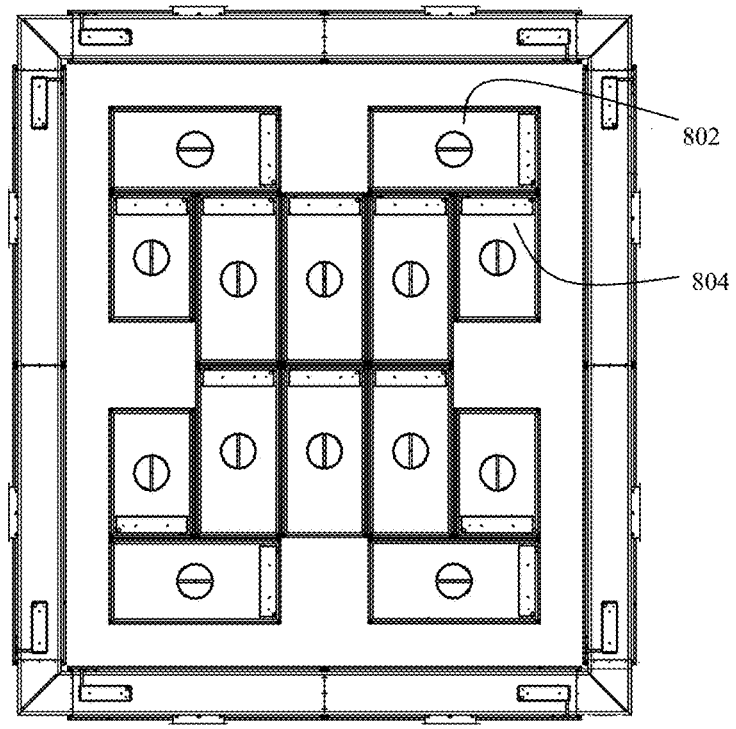
FIG. 8B shows a view of the interior of the laminar array portion of the ceiling mounted structural device when all of the perforated panels of its various laminar air flow systems have been removed.

FIG. 8B shows a view of the plenum which provides air to the laminar array. Essentially, this can also be considered to be a view of a portion of the interior of the ceiling mounted structural device (101) when all of the perforated panels (102a) of the mounted laminar air flow systems have been removed. Each laminar air flow system (102) has its own damper and air supply connection (802). Note that dampers (802) need not be equipped with actuators, and need not be computer operated dampers (although in some embodiments, they may be) since air to the system can be controlled by other dampers, such as damper BTD-1 shown in FIG. 3.

Some details of the LED drivers (804) used to drive the LED lighting system are also shown.

Figure 9C:
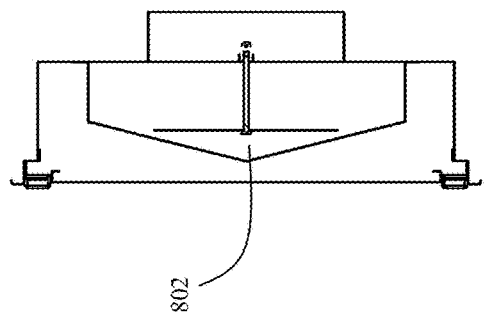
FIG. 9C shows a short axis side view of an individual laminar air flow system module. This shows a detail of the air supply connection and damper from a different perspective.
Figure 9A:
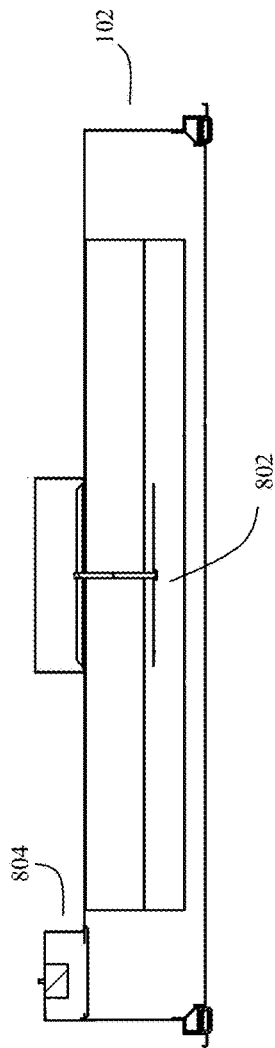
FIG. 9A shows a long axis side view of an individual laminar air flow system module. Here more details of the air supply connection and damper and the LED drivers (used to power the system's Light Emitting Diodes) may be seen.

FIG. 9A shows a long axis side view of an individual laminar air flow system module (102). Here more details of the air supply connection and damper (802) and the LED drivers (804) may be seen. In some embodiments, modules such as the Krueger Sterilfo System®, Sterilflex™ system, or alternative systems, may be used.

In some embodiments, the laminar air flow system may also include UV lights configured to provide further UV sterilization to the incoming HEPA filtered air. In some embodiments, UV sterilizing systems such as Steril-Aire UVC emitter system system, produced by Steril-Aire, Inc. may be used.

Figure 9B:
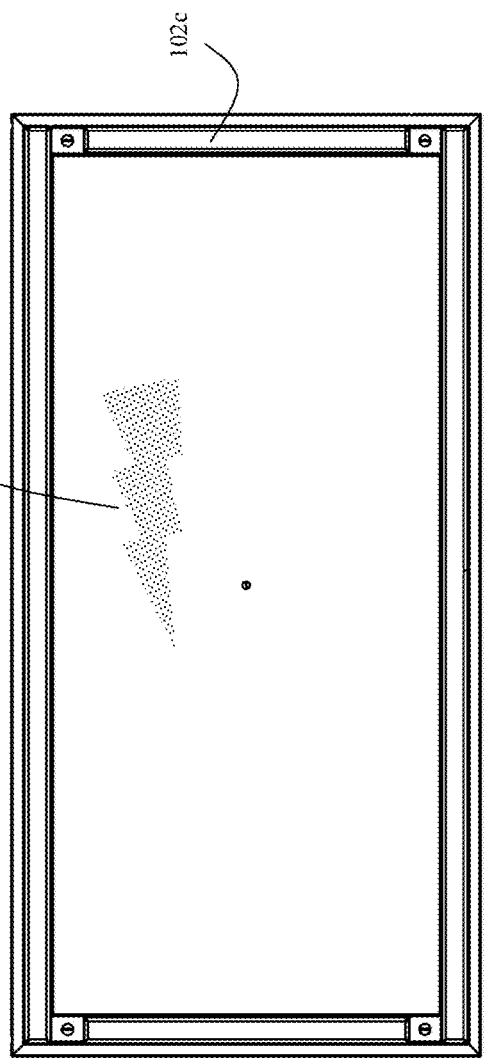
FIG. 9B shows a view looking up at the face of an individual air flow system module. Here details of the perforated wall structure and LED lighting may be seen.

FIG. 9B shows a view looking up at the face of an individual air flow system module (102). Here details of the perforated wall structure (102a) and LED lighting (102) may be seen.

FIG. 9C shows a short axis side view of an individual laminar air flow system module (102). This shows a detail of the air supply connection and damper (802) from a different perspective.

Sterilflex™ is a trademark, and Sterilfo System® is a registered trademark, of Lau Industries, Inc., a Delaware Corporation.

The invention claimed is:

1. A method of reducing a risk of HAI, method comprising:
    verifying that no humans are present in a healthcare chamber and restricting access to said chamber, said chamber comprising air impermeable chamber walls, ceiling, and floor;
    isolating the interior air flow in said chamber from outside air by closing at least one return damper and at least one supply air damper;
    wherein said chamber is configured to return interior air from said chamber using said at least one return air damper, and wherein said chamber is configured to obtain interior air by obtaining sterilized outside air, said sterilized outside air obtained by using a ceiling mounted structural device comprising a load bearing structure, and a laminar air flow system mounted on said structural device, to blow HEPA filtered and UV sterilized supply air over a defined field in said chamber, said laminar air flow system connected to said at least one supply air damper;
    activating an air phase anti-microbial agent generator, said generator configured to fill said chamber with air phase anti-microbial agents at a time and dose level configured to kill at least a substantial majority of microbes in said chamber;
    deactivating said generator, and to flushing remaining air phase anti-microbial agents from said chamber by at least opening said return damper and said at least one supply damper.

2. The method of claim 1, wherein said air phase anti-microbial agent generator is a combination generator and humidifier that operates by regulating humidity, and converting an aqueous solution of hydrogen peroxide into air phase hydrogen peroxide by using any of a misting, nebulizer based, vaporizing based, or aerosol generating type process.

3. The method of claim 1, wherein at least the substantial majority of said chamber's walls are covered with materials selected to be resistant to said air phase anti-microbial agents, said materials comprising any of glass, list of other not so common materials.

4. The method of claim 1, wherein said chamber is an operating room, said defined field in said chamber is an operating table; and
    said ceiling mounted structural device has a polygonal shape configured with a plurality of internal grids, at least some of said grids configured to accommodate electrical conduits and to supply structural support for standard operating room boom mounted equipment.

5. The method of claim 4, wherein said laminar air flow system further comprises a plurality of air curtains that produce a plurality of directionally-controlled airstreams configured to reduce penetration of particles from outside an area of said operating table to inside an area of said operating table.

6. The method of claim 5, wherein exterior dimensions of said polygonal shape exceed exterior dimensions of the operating table;
    said polygonal shape is a rectangular polygonal shape, said plurality of air curtains extends on all four sides of a perimeter of said rectangular polygonal shape so as to exceed said exterior dimensions of said operating table, and to isolate said operating table from airborne particles outside of said operating table; and
    wherein said laminar air flow system is disposed on an interior of said rectangular shape and introduces an air flow configured to flush airborne particles from the area of said operating table to an area outside said operating table;
    at least some of said internal grids are configured to accommodate electrical conduits with widths of at least 2 inches; and
    wherein at least some of said internal grids comprise weigh supporting flanges configured to supply structural support for said standard operating room boom mounted equipment.

7. The method of claim 1, further comprising:
    using at least one computer processor to verify that no humans are present in a healthcare chamber and to restrict access to said chamber;
    using said at least one computer processor to isolate interior air flow in said chamber from outside air by closing at least one computer controlled return damper and at least one computer controlled supply air damper;
    wherein said chamber is configured to return interior air from said chamber using said at least one computer controlled return air damper;
    said laminar air flow system connected to said at least one computer controlled supply air damper;
    using said at least one computer processor to activate an air phase anti-microbial agent generator;
    using said at least one computer processor to deactivate said generator, and to flush remaining air phase anti-microbial agents from said chamber by at least opening said computer controlled return damper and said at least one computer controlled supply damper.

8. The method of claim 7, wherein said chamber is equipped with at least one-way computer operated door locks, and wherein using said at least one computer processor to restrict access to said chamber comprises setting said at least one-way computer door locks to restrict humans outside said chamber from entering said chamber.

9. The method of claim 8, wherein said chamber is equipped with at least one sensor configured to monitor amounts of air-phase anti-microbial agents present in said air, said at least one sensor transmits data to said at least one processor, and wherein said at least one processor is configured to set said at least one-way computer door locks to allow humans to enter said chamber only after said at least one sensor reports that said air phase anti-microbial agents are at a non-toxic level.

10. The method of claim 7, wherein using said at least one computer processor to verify that no humans are present in said chamber comprises using said at least one computer processors to sample a plurality of different occupancy sensors, said plurality of different occupancy sensors comprising any of motion sensors, infrared sensors, video cameras, carbon dioxide sensors, and sound sensors.

11. The method of claim 7, wherein said at least one computer processor is controlled by at least one touch panel equipped graphical user interface terminal mounted either on an interior chamber wall, and/or exterior to said chamber.

12. The method of claim 7, further using said at least one computer processor to turn on at least one fan to further flush remaining air phase anti-microbial agents from said chamber, and/or further using at least one computer controlled catalyst damper and a catalyst to deactivate any remaining air-phase anti-microbial agents.

13. A method of reducing a risk of HAI, said method comprising:
using at least one computer processor to verify that no humans are present in a healthcare chamber and to restrict access to said chamber, said chamber comprising air impermeable chamber walls, ceiling, and floor;
wherein using said at least one computer processor to verify that no humans are present in said chamber comprises using said at least one computer processors to sample a plurality of different occupancy sensors, said plurality of different occupancy sensors comprising any of motion sensors, infrared sensors, video cameras, carbon dioxide sensors, and sound sensors;
using said at least one computer processor to isolate interior air flow in said chamber from outside air by closing at least one computer controlled return damper and at least one computer controlled supply air damper;
wherein said chamber is configured to return interior air from said chamber using said at least one computer controlled return air damper, and wherein said chamber is configured to obtain interior air by obtaining sterilized outside air, said sterilized outside air obtained by using a ceiling mounted structural device comprising a load bearing structure, and a laminar air flow system mounted on said structural device, to blow HEPA filtered and UV sterilized supply air over a defined field in said chamber, said laminar air flow system connected to said at least one computer controlled supply air damper;
wherein said chamber is an operating room, said defined field in said chamber is an operating table; and
said ceiling mounted structural device has a polygonal shape configured with a plurality of internal grids, at least some of said grids configured to accommodate electrical conduits and to supply structural support for standard operating room boom mounted equipment;
wherein said laminar air flow system further comprises a plurality of air curtains that produce a plurality of directionally-controlled airstreams configured to reduce penetration of particles from outside an area of said operating table to inside said area of said operating table;
using said at least one computer processor to activate an air phase anti-microbial agent generator, said generator configured to fill said chamber with air phase anti-microbial agents at a time and dose level configured to kill at least a substantial majority of microbes in said chamber;
wherein said air phase anti-microbial agent generator is a combination generator and humidifier that operates by regulating humidity, and converting an aqueous solution of hydrogen peroxide into air phase hydrogen peroxide by using any of a misting, nebulizer based, vaporizing based, or aerosol generating type process;
using said at least one computer processor to deactivate said generator, and to flush remaining air phase anti-microbial agents from said chamber by at least opening said computer controlled return damper and said at least one computer controlled supply damper.

14. The method of claim 13, wherein exterior dimensions of said polygonal shape exceed exterior dimensions of the operating table;
said polygonal shape is a rectangular polygonal shape, said plurality of air curtains extends on all four sides of a perimeter of said rectangular polygonal shape so as to exceed said exterior dimensions of said operating table, and to isolate said operating table from airborne particles outside of said operating table; and
wherein said laminar air flow system is disposed on an interior of said rectangular shape and introduces an air flow configured to flush airborne particles from the area of said operating table to an area outside said operating table;
at least some of said internal grids are configured to accommodate electrical conduits with widths of at least 2 inches; and
wherein at least some of said internal grids comprise weigh supporting flanges configured to supply structural support for said standard operating room boom mounted equipment.

15. The method of claim 13, wherein said chamber is equipped with at least one-way computer operated door locks, and wherein using said at least one computer processor to restrict access to said chamber comprises setting said at least one-way computer door locks to restrict humans outside said chamber from entering said chamber.

16. The method of claim 15, wherein said chamber is equipped with at least one sensor configured to monitor amounts of air-phase anti-microbial agents present in said air, said at least one sensor transmits data to said at least one processor, and wherein said at least one processor is configured to set said at least one-way computer door locks to allow humans to enter said chamber only after said at least one sensor reports that said air phase anti-microbial agents are at a non-toxic level.

17. The method of claim 13, wherein at least the majority of said chamber's walls are covered with materials selected to be resistant to said air phase anti-microbial agents, said materials comprising any of glass and stainless steel.

18. The method of claim 17, wherein said materials comprise computer configurable display screens configured to display images generated by either said at least one computer processor or from other digital image sources.

19. The method of claim 13, wherein said at least one computer processor is controlled by at least one touch panel equipped graphical user interface terminal mounted either on an interior chamber wall, and/or exterior to said chamber.

20. The method of claim 13, further using said at least one computer processor to turn on at least one fan to further flush remaining air phase anti-microbial agents from said chamber, and/or further using at least one computer controlled catalyst damper and a catalyst to deactivate any remaining air-phase anti-microbial agents.

* * * * *